US010857074B2

(12) United States Patent
Lee et al.

(10) Patent No.: US 10,857,074 B2
(45) Date of Patent: Dec. 8, 2020

(54) METHOD FOR PREPARING STICK-TYPE COSMETIC COMPOSITION

(71) Applicant: KOLMAR KOREA CO., LTD., Sejong-si (KR)

(72) Inventors: Jin Sung Lee, Seoul (KR); Jin Mo Kim, Seoul (KR); Sung Chun Lee, Seoul (KR)

(73) Assignee: KOLMAR KOREA CO., LTD., Sejong-si (KR)

( * ) Notice: Subject to any disclaimer, the term of this patent is extended or adjusted under 35 U.S.C. 154(b) by 0 days.

(21) Appl. No.: 16/342,751

(22) PCT Filed: Nov. 10, 2017

(86) PCT No.: PCT/KR2017/012712
§ 371 (c)(1),
(2) Date: Apr. 17, 2019

(87) PCT Pub. No.: WO2018/088831
PCT Pub. Date: May 17, 2018

(65) Prior Publication Data
US 2019/0231652 A1    Aug. 1, 2019

(30) Foreign Application Priority Data

Nov. 11, 2016 (KR) ........................ 10-2016-0150262
Nov. 1, 2017 (KR) ........................ 10-2017-0144655

(51) Int. Cl.
| | | |
|---|---|---|
| *A61K 8/02* | (2006.01) | |
| *A61K 8/04* | (2006.01) | |
| *A61K 8/34* | (2006.01) | |
| *A61K 8/37* | (2006.01) | |
| *A61K 8/92* | (2006.01) | |
| *A61K 8/96* | (2006.01) | |
| *A61Q 17/04* | (2006.01) | |
| *A61K 8/26* | (2006.01) | |
| *A61Q 1/02* | (2006.01) | |
| *A61Q 1/06* | (2006.01) | |

(52) U.S. Cl.
CPC .......... *A61K 8/0204* (2013.01); *A61K 8/0229* (2013.01); *A61K 8/04* (2013.01); *A61K 8/26* (2013.01); *A61K 8/345* (2013.01); *A61K 8/37* (2013.01); *A61K 8/92* (2013.01); *A61K 8/922* (2013.01); *A61K 8/965* (2013.01); *A61Q 1/02* (2013.01); *A61Q 17/04* (2013.01); *A61Q 1/06* (2013.01)

(58) Field of Classification Search
CPC .................................................. A61K 8/0229
See application file for complete search history.

(56) References Cited

U.S. PATENT DOCUMENTS

| | | | | |
|---|---|---|---|---|
| 6,183,760 B1 * | 2/2001 | Travkina | .................. | A61K 8/29 424/401 |
| 7,037,511 B1 * | 5/2006 | Gers-Barlag | ............ | A61K 8/02 424/401 |
| 2008/0070993 A1 * | 3/2008 | Borbely | ................. | A61K 8/735 514/777 |
| 2016/0206527 A1 * | 7/2016 | Hueber | .................. | A61K 8/025 |

FOREIGN PATENT DOCUMENTS

| | | |
|---|---|---|
| KR | 10-2006-0070845 A | 6/2006 |
| KR | 10-0789345 B1 | 12/2007 |
| KR | 10-2011-0059404 A | 6/2011 |
| KR | 10-1054884 B1 | 8/2011 |
| KR | 10-2013-0046272 A | 5/2013 |
| KR | 10-2015-0076858 A | 7/2015 |
| KR | 10-2016-0102762 A | 8/2016 |

OTHER PUBLICATIONS

Office action dated May 28, 2019 from Korean Patent Office in a counterpart Korean Patent Application No. 10-2017-0144655 (all the cited references are listed in this IDS.) (English translation is submitted herewith.).
International Search Report for PCT/KR2017/012712 dated Mar. 28, 2018.
Product Information, Chapstick Real Original (Pfizer Pharmaceuticals Korea Ltd.), Jun. 3, 2016, <URL: https://www.pfizerco.kr/ko/products/chapstick-real-original-%EC%B1%95%EC%8A%A4%ED%8B%B1-%EB%A6AC%EC%96%BC-%EC%98%A4%EB%A6%AC%EC%A7%80%EB'1c.84%90> See the inactive ingredients. (English translation is also submitted herewith.).
Notice of Allowance dated Mar. 30, 2020 from Korean Patent Office in a counterpart Korean Patent Application No. 10-2017-0144655 (all the cited references are listed in this IDS.) (English translation is submitted herewith.).

* cited by examiner

*Primary Examiner* — Kyle A Purdy
(74) *Attorney, Agent, or Firm* — The PL Law Group, PLLC (57) ABSTRACT

A method of preparing a stable stick-type cosmetic composition includes separately stabilizing a clay mineral dispersion and a moisturizing component, thereby uniformly dispersing components in the composition. In a typical stick-type composition, components are not uniformly dispersed, and thus a stick formulation prepared using the same is easily broken upon external impact or the like, but the stick formulation prepared by the method of the present invention is maintained in spreadability and sensation of use, and is not easily broken.

18 Claims, 4 Drawing Sheets

METHOD FOR PREPARING STICK-TYPE COSMETIC COMPOSITION

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/012712, filed on Nov. 10, 2017, which claims priority to the benefit of Korean Patent Application No. 10-2016-0150262 filed on Nov. 11, 2016 and 10-2017-0144655 filed on Nov. 1, 2017 in the Korean Intellectual Property Office, the entire contents of which are incorporated herein by reference.

TECHNICAL FIELD

The present invention relates to a method of preparing a stable stick-type cosmetic composition and a stick-type cosmetic composition prepared using the same.

BACKGROUND ART

Stick-type cosmetics are easy to use and are very portable, and thus the application fields thereof, including as sunscreens, stick-type foundations and the like, as well as lipstick, which is a typical stick-type cosmetic, are broadening.

However, stick-type cosmetics have a problem in that they are easily broken by external impact or upon application to the skin due to the intrinsic limitations of components of cosmetic compositions. With the goal of solving the above problem, attempts have been made to increase the amount of wax or the like in the cosmetic composition. However, when the amount of wax is increased, the strength of formulations is excessively increased, undesirably causing lowered skin spreadability and discomfort of a user owing to the unique smell of wax or the like. Furthermore, there are known stick-type formulations in which a material having superior mechanical properties is disposed at the central portion thereof and a cosmetic composition is disposed therearound. However, these methods do not solve the intrinsic limitations of cosmetic compositions, and have problems in which the cosmetic composition is separated from the central portion, or in which some cracking and peeling may occur.

SUMMARY

Accordingly, the present invention is intended to provide a method of uniformly dispersing components contained in a stick-type cosmetic composition.

In addition, the present invention is intended to provide a stick-type cosmetic composition, which is capable of maintaining skin spreadability and is also not easily breakable.

An aspect of the present invention provides a method of preparing a stick-type cosmetic composition, the method comprising a first stabilization step of forming a clay mineral dispersion by mixing 0.01 to 7 wt % of a clay mineral and 0.05 to 35 wt % of a first emollient based on the total weight of the composition; a second stabilization step of forming a moisturizing component dispersion by mixing 0.01 to 45 wt % of a moisturizing component and 0.01 to 10 wt % of a first surfactant based on the total weight of the composition; and a step of adding the clay mineral dispersion and the moisturizing component dispersion to an oil-phase part.

Another aspect of the present invention provides a stick-type cosmetic composition prepared by the above method.

According to the present invention, a method of preparing a stick-type cosmetic composition comprises separately stabilizing a clay mineral dispersion and a moisturizing component, thereby uniformly dispersing components in the composition. In a typical stick-type composition, components are not uniformly dispersed and thus the resulting formulation breaks easily due to separation between components therein, but the stick-type cosmetic composition prepared by the method of the present invention is capable of maintaining spreadability and the sensation of use and is also not easily breakable.

DETAILED DESCRIPTION

Hereinafter, a detailed description will be given of the present invention.

As used herein, the terms "first" and "second" are used to distinguish individual components and preparation steps, and are not used to limit the sequence of addition or mixing of components or the sequence of preparation steps.

An aspect of the present invention pertains to a method of preparing a stick-type cosmetic composition, the method comprising a first stabilization step of forming a clay mineral dispersion by mixing 0.01 to 7 wt % of a clay mineral and 0.05 to 35 wt % of a first emollient based on the total weight of the composition; a second stabilization step of forming a moisturizing component dispersion by mixing 0.01 to 45 wt % of a moisturizing component and 0.01 to 10 wt % of a first surfactant based on the total weight of the composition; and a step of adding the clay mineral dispersion and the moisturizing component dispersion to an oil-phase part.

In the method of preparing the stick-type cosmetic composition according to the aspect of the present invention, the clay mineral and the moisturizing component are separately subjected to a stabilization process, and are then mixed with the oil-phase part including wax and the like, whereby the clay component and the moisturizing component are uniformly dispersed in the composition and thus the resulting product is not easily breakable. In particular, a stick-type cosmetic composition is configured such that components contained in the composition precipitate to a lower portion in the height direction of a formulation according to Stoke's law due to the unidirectionally elongated shape, and are thus non-uniformly distributed in the composition. When the composition contains the clay mineral, the viscosity of the composition may increase, thus decreasing the rate of precipitation of components in the composition. Furthermore, when the first stabilization step and/or the second stabilization step according to the present invention are performed, the clay mineral and the moisturizing component are uniformly dispersed in the composition and thus each particle size is decreased, thereby reducing the rate of precipitation. As for the composition according to the aspect of the present invention, the rate of precipitation of the components in the composition may decrease, and thus non-uniform distribution of the components in the composition may be minimized, and moreover, separation of the components in the formulation may be minimized, thereby reducing breakage of the formulation.

In the above aspect, the step of adding the clay mineral dispersion and the moisturizing component dispersion to the oil-phase part may include adding the clay mineral dispersion to the oil-phase part and then adding the moisturizing component dispersion thereto.

In particular, when the moisturizing component is a water-soluble material, formulation stability may become problematic due to separation thereof from the oil component. In an embodiment of the present invention, since the moisturizing component is first stabilized and thus uniformly dispersed in the composition, separation of the formulation may be minimized, and breakage of the formulation may be reduced.

In the above aspect, the clay mineral is contained in an amount of 0.01 to 7 wt %, preferably 0.03 to 6 wt %, and more preferably 0.05 to 5 wt %. If the amount of the clay mineral is less than 0.05 wt % based on the total weight of the composition, stable interactions with the moisturizing component may become impossible, and thus the moisturizing component may become lumpy and the stick-type formulation may break down. On the other hand, if the amount of the clay mineral exceeds 5 wt %, the sensation of use of the stick-type cosmetic composition may become stiff and the moisturizing capacity is lowered.

In the above aspect, the first emollient is contained in an amount of 0.05 to 35 wt %, preferably 0.3 to 30 wt %, and more preferably 0.25 to 25 wt %, based on the total weight of the composition.

Also, in the above aspect, the first emollient may be contained in an amount of 300 to 1000 parts by weight based on 100 parts by weight of the total weight of the clay mineral. If the amount of the first emollient is less than 300 parts by weight based on 100 parts by weight of the total weight of the clay mineral, the clay mineral cannot be uniformly dispersed in the composition, thus deteriorating formulation stability. The first emollient is preferably contained in an amount of 500 to 1000 parts by weight based on 100 parts by weight of the total weight of the clay mineral.

In the above aspect, the first emollient may include, but is not limited to, caprylic capric triglyceride.

In the above aspect, the moisturizing component is contained in an amount of 0.01 to 45 wt %, preferably 0.05 to 40 wt %, and more preferably 0.1 to 35 wt % based on the total weight of the composition. If the amount of the moisturizing component is less than 0.1 wt %, the moisturizing capacity of the cosmetic composition may be remarkably decreased. On the other hand, if the amount thereof exceeds 35 wt %, a phenomenon of separation in the formulation may occur, and thus the formulation stability of the cosmetic composition may decrease.

In the above aspect, the moisturizing component may be a water-soluble moisturizing component. In an embodiment, the moisturizing component may include glycerin.

Also, in the above aspect, the first surfactant is contained in an amount of 0.01 to 10 wt %, preferably 0.05 to 7 wt %, and more preferably 0.1 to 5 wt %, based on the total weight of the composition. If the amount of the first surfactant is less than 0.1 wt %, the moisturizing component cannot be stably dispersed and emulsified, and thus a separation phenomenon may occur. On the other hand, if the amount thereof exceeds 5 wt %, the moisturizing component is not finely dispersed but lumps, making it impossible to uniformly disperse the moisturizing component in the cosmetic composition. For example, if the amount of the first surfactant exceeds 5 wt %, the moisturizing-component-containing material may have an average particle size of greater than 10 µm, making it impossible to uniformly disperse the moisturizing component in the cosmetic composition.

As used herein, the moisturizing-component-containing material may include a material containing only the moisturizing component or a material containing not only the moisturizing component but also other components.

As used herein, the average particle size may refer to the average length of two axes measured from arbitrary points, other than the longest and shortest axes of the particle diameter.

In the above aspect, the first surfactant may include cetearyl olivate, sorbitan olivate or a mixture thereof.

In an embodiment, the clay mineral may include a platelet-shaped mineral. Specifically, the platelet-shaped mineral may include smectite. Smectite may include hectorite or bentonite, and preferably comprises hectorite. In an embodiment, when the clay mineral is hectorite, the components in the stick-type cosmetic composition are most uniformly dispersed, and the physical strength of the stick-type cosmetic composition is excellent.

In an embodiment, the clay mineral may be stearalkonium hectorite.

Also, in the above aspect, the first stabilization step may include stirring the clay mineral and the first emollient at 1000 to 2500 rpm, and preferably at 1500 to 2000 rpm. If the stirring rate in the first stabilization step is less than 1000 rpm, the clay mineral does not sufficiently swell in the first emollient, and thus viscosity necessary to obtain a stable formulation cannot be ensured. On the other hand, if the stirring rate in the first stabilization step exceeds 2500 rpm, excessive foaming may occur in the composition, undesirably deteriorating formulation stability.

Also, in the above aspect, the second stabilization step may include mixing the moisturizing component and the first surfactant at 60 to 90° C. The second stabilization step is preferably performed at 75 to 85° C. If the temperature of the second stabilization step is lower than 60° C., the surfactant in a solid phase cannot be dissolved. On the other hand, if the temperature thereof is higher than 90° C., components in the composition may be thermally deformed or volatilized and thus released.

As used herein, the temperature is expressed in degrees Celsius unless otherwise indicated.

In an embodiment, the oil-phase part may include, based on the total weight of the composition, 5 to 40 wt % of wax, 0.01 to 10 wt % of a second surfactant, and the remainder of a second emollient, which are mixed together.

In an embodiment, the oil-phase part may further include butter or a preservative. The butter is contained in an amount of 1 to 5 wt %, and preferably 2.5 to 3.5 wt %, based on the total weight of the composition. The butter may include, but is not limited to, mango butter, Shea butter, cocoa butter, or jojoba butter.

Furthermore, the preservative is contained in an amount of 0.03 to 1.5 wt %, and preferably 0.05 to 1.3 wt %, based on the total weight of the composition. The preservative may include, but is not limited to, ethylhexyl glycerin or 1,2-hexanediol.

In the above aspect, the wax is contained in an amount of 5 to 40 wt %, preferably 6 to 35 wt %, and more preferably 10 to 30 wt %, based on the total weight of the composition. If the amount of wax is less than 10 wt % based on the total weight of the composition, it is difficult to form a stick-type formulation. On the other hand, if the amount thereof exceeds 30 wt %, the strength is too high and thus spreadability, particularly spreadability on the lips, may decrease.

In the above aspect, the wax may include, but is not limited to, at least one selected from the group consisting of carnauba wax, candelilla wax, propolis wax, ozokerite, microcrystalline wax, and beeswax.

Also, in the above aspect, the second surfactant is contained in an amount of 0.01 to 10 wt %, preferably 0.05 to 8 wt %, and more preferably 0.1 to 7 wt %. If the amount of the second surfactant is less than 0.1 wt %, components in the composition cannot be stably and uniformly dispersed and emulsified. On the other hand, if the amount thereof exceeds 7 wt %, formulation separation may occur.

In the above aspect, the second surfactant may include, but is not limited to, cetyl PEG/PPG-10/1-dimethicone or sorbitan olivate.

In the above aspect, the second emollient may include, but is not limited to, at least one selected from the group consisting of *Macadamia ternifolia* seed oil, pentaerythrityl tetraisostearate, and caprylic capric triglyceride.

Another aspect of the present invention pertains to a stick-type cosmetic composition prepared using the above method.

The cosmetic composition may be a composition for lips. It is difficult to produce a stick formulation for lips having adequate spreadability due to the specific structural characteristics of the lips themselves (e.g., lips have a large volume relative to the area thereof and do not have structures such as bones therein). The stick-type cosmetic composition according to the aspect of the present invention is able to maintain optimal spreadability and is not easily broken when applied to the lips.

The stick-type cosmetic composition may be for lip makeup, lip moisturizing or skin makeup. For example, the stick-type cosmetic composition may be a lipstick or a lip gloss, but is not limited thereto. Also, the composition for skin makeup may include, but is not limited to, a stick-type sunscreen, a stick-type foundation, or a stick-type cleanser.

A better understanding of the configuration and effects of the present invention will be given through the following examples and test examples. However, these examples and test examples are merely set forth to illustrate the present invention and are not to be construed as limiting the spirit and scope of the present invention.

[Example 1] Preparation of Stick-Type Cosmetic Composition

[Example 1-1] Stabilization of Clay Mineral 2 wt % of stearalkonium hectorite and 10 wt % of caprylic/capric triglyceride based on the total weight of the composition were stirred at 1500 to 2000 rpm for 30 min using a high-speed stirrer, whereby the clay mineral was first dispersed in the emollient and thus stabilized.

[Example 1-2] Stabilization of Moisturizing Component 10 wt % of glycerin and 3 wt % of cetearyl olivate/sorbitan olivate based on the total weight of the composition were dissolved at 75 to 85° C. and then emulsified using a high-speed homogenizer, whereby glycerin was dispersed and thus stabilized.

[Example 1-3] Preparation of Oil-Phase Part and Stick-Type Formulation

Components shown in Table 1 below were mixed at 80 to 85° C. to afford an oil-phase part. Thereafter, the stabilized clay mineral of Example 1-1 was added to the oil-phase part and stirred and dispersed using a homogenizer.

Thereafter, the stabilized glycerin-cetearyl olivate/sorbitan olivate of Example 1-2 was added thereto and stirred and dispersed using a homogenizer, thereby preparing a composition. Thereafter, foam in the composition was removed and impurities were filtered, ultimately obtaining a composition, which was then prepared into a stick-type formulation.

TABLE 1

| Oil-phase part | Wax | Candelilla wax | 7 wt % |
|---|---|---|---|
| | Wax | Ozokerite | 3 wt % |
| | Wax | Microcrystalline wax | 3 wt % |
| | Wax | Beeswax | 2 wt % |
| | Emollient | *Macadamia integrifolia* seed oil | 23.95 wt % |
| | Emollient | Pentaerythrityl tetraisostearate | 15 wt % |
| | Emollient | Caprylic/capric triglyceride | 15 wt % |
| | Surfactant | Cetyl PEG/PPG-10/1-dimethicone | 2 wt % |
| | Surfactant | Sorbitan olivate | |
| | Butter | Shea butter | 3 wt % |
| | Preservative | Ethylhexyl glycerin | 0.05 wt % |
| | Preservative | 1,2-hexanediol | 1 wt % |

[Test Example 1] Measurement of Properties of Stick-Type Formulation

Panel tests were conducted on the sensation of use (soft sensation, moisturizing sensation, moisturizing persistence and formulation stability) of 50 female and 50 male panelists. The stick formulation prepared in Example 1 was applied in an amount of 0.1 g on lips that had been rinsed with water and dried, and after 1 min, the sensation of use was evaluated. Shape stability was evaluated for breakage, crushing, or formulation stability during application to the lips. The evaluation results were scored in the range from 5 points to 1 point, including 5 points when the sensation of use was excellent and 1 point when it was very poor, and the average of the sum of the scores of individual panelists was calculated. The results are shown in Table 2 below.

[Comparative Example 1] Comparison with Stick-Type Formulation not Subjected to Stabilization Step

[Comparative Example 1-1] Upon Performing Neither Stabilization of Clay Mineral Nor Stabilization of Moisturizing Component A typical stick-type formulation was prepared by mixing the same components as in Example 1 together, with the exception that the clay mineral and the surfactant used for the stabilization step of Example 1 were not used. The typical stick-type formulation was subjected to the panel test for the sensation of use in the same manner as in Test Example 1. The results are shown in Table 2 below.

TABLE 2

| Classification | Comparative Example 1-1 | Test Example 1 |
|---|---|---|
| Soft sensation | 3.6 | 4.2 |
| Moisturizing sensation (water) | 2.8 | 4.0 |
| Moisturizing sensation (oil) | 3.32 | 3.48 |
| Moisturizing persistence | 3.82 | 3.91 |
| Shape stability | 1.53 | 3.82 |

Evaluation criteria:
excellent 5,
good 4,
fair 3,
poor 2,
very poor 1

Figure 1A:
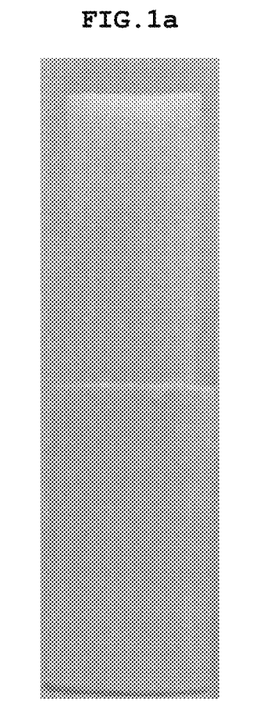
FIGS. 1a and 1b are a photograph and a schematic view of the lateral side of a stick-type formulation according to an aspect of the present invention.
Figure 1B:
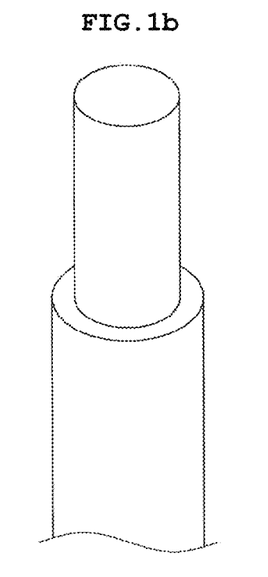
Figure 2A:
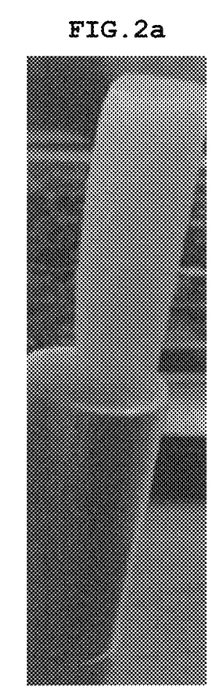
FIGS. 2a and 2b are a photograph and a schematic view of the lateral side of a stick-type formulation (Comparative Example 1-1) in which neither a clay mineral nor a moisturizing component are stabilized.
Figure 2B:
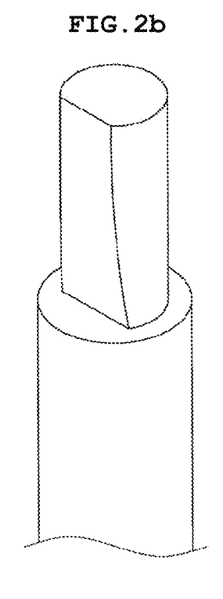

As is apparent from Table 2, the stick formulation of the present invention subjected to the stabilization step was very superior in the sensation of use compared to the typical stick formulation not subjected to the stabilization step. In particular, shape stability was about 2.5 times or more thereof (FIGS. 2a and 2b).

Figure 3A:
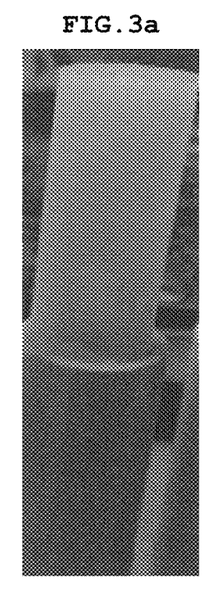
FIGS. 3a and 3b are a photograph and a schematic view of the lateral side of a stick-type formulation (Comparative Example 1-2) in which only a clay mineral is stabilized.
Figure 3B:
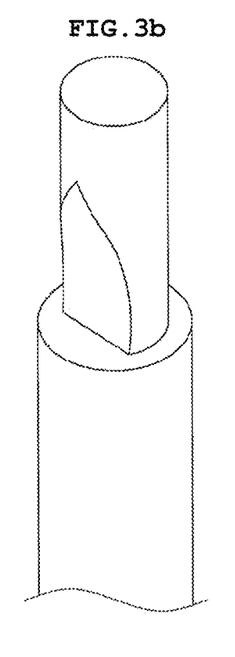

[Comparative Example 1-2] Upon Performing Stabilization of Clay Mineral without Stabilization of Moisturizing Component A stick-type formulation was prepared in the same manner as in Example 1, with the exception that the moisturizing component of Example 1-2 was not stabilized. Thereafter, the properties of the stick-type formulation were measured in the same manner as in Test Example 1. The results are shown in Table 3 below. As such, the physical stability of the stick was significantly decreased due to the precipitation of glycerin (FIGS. 3a and 3b).

TABLE 3

| Classification | Comparative Example 1-2 | Test Example 1 |
|---|---|---|
| Soft sensation | 3.9 | 4.2 |
| Moisturizing sensation (water) | 3.4 | 4.0 |
| Moisturizing sensation (oil) | 3.3 | 3.48 |
| Moisturizing persistence | 3.5 | 3.91 |
| Shape stability | 2.3 | 3.82 |

Evaluation criteria:
excellent 5,
good 4,
fair 3,
poor 2,
very poor 1

[Comparative Example 1-3] Upon Performing Stabilization of Moisturizing Component without Stabilization of Clay Mineral A stick-type formulation was prepared in the same manner as in Example 1, with the exception that the clay mineral of Example 1-1 was not stabilized. Thereafter, the properties of the stick-type formulation were measured in the same manner as in Test Example 1. The results are shown in Table 4 below. As such, the physical stability of the stick was significantly decreased due to the precipitation of glycerin. Here, the lateral side view of the stick-type formulation was similar to FIGS. 3a and 3b.

TABLE 4

| Classification | Comparative Example 1-3 | Test Example 1 |
|---|---|---|
| Soft sensation | 3.7 | 4.2 |
| Moisturizing sensation (water) | 3.2 | 4.0 |
| Moisturizing sensation (oil) | 3.35 | 3.48 |
| Moisturizing persistence | 3.6 | 3.91 |
| Shape stability | 2.5 | 3.82 |

Evaluation criteria:
excellent 5,
good 4,
fair 3,
poor 2,
very poor 1

[Comparative Example 2] Properties of Stick-Type Formulation Depending on Preparation Sequence Comparative Example 2-1

Figure 4A:
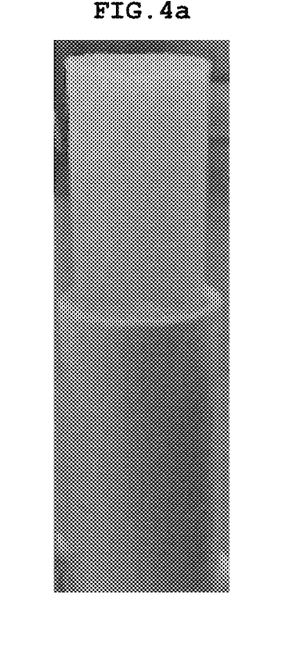
FIGS. 4a and 4b are a photograph and a schematic view of the lateral side of a stick-type formulation (Comparative Example 2-1) in which stearalkonium hectorite, caprylic/capric triglyceride, and cetearyl olivate/sorbitan olivate are added together to an oil-phase part and then glycerin is added thereto.
Figure 4B:
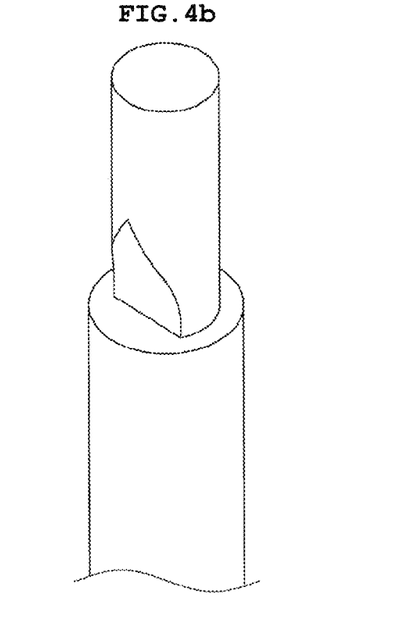

Unlike Example 1, 2 wt % of stearalkonium hectorite, 10 wt % of caprylic/capric triglyceride, and 3 wt % of cetearyl olivate/sorbitan olivate were added together to an oil-phase part, after which 10 wt % of glycerin was added thereto, thereby preparing a stick-type formulation. Thereafter, the properties of the stick-type formulation were measured as in Test Example 1. As such, the physical stability of the stick was greatly decreased because glycerin was not stabilized (FIGS. 4a and 4b).

TABLE 5

| Classification | Comparative Example 2-1 | Test Example 1 |
|---|---|---|
| Soft sensation | 3.6 | 4.2 |
| Moisturizing sensation (water) | 2.8 | 4.0 |
| Moisturizing sensation (oil) | 3.32 | 3.48 |
| Moisturizing persistence | 3.82 | 3.91 |
| Shape stability | 1.53 | 3.82 |

Evaluation criteria:
excellent 5,
good 4,
fair 3,
poor 2,
very poor 1

Comparative Example 2-2

A stick-type formulation was prepared in the sequence opposite that of Comparative Example 2-1, and tested in the same manner as in Test Example 1. The results are shown in Table 6 below. As such, the formulation was too soft and the components contained in the formulation were non-uniformly distributed in the height direction of the stick-type formulation, and thus the physical stability of the stick was greatly decreased. The outer appearance observed from the lateral side was very similar to FIGS. 4a and 4b.

TABLE 6

| Classification | Comparative Example 2-1 | Test Example 1 |
|---|---|---|
| Soft sensation | 3.65 | 4.2 |
| Moisturizing sensation (water) | 3.6 | 4.0 |
| Moisturizing sensation (oil) | 3.35 | 3.48 |
| Moisturizing persistence | 3.8 | 3.91 |
| Shape stability | 2.4 | 3.82 |

Evaluation criteria:
excellent 5,
good 4,
fair 3,
poor 2,
very poor 1

[Comparative Example 3] Properties of Stick-Type Formulation Depending on Component Content Stick-type formulations were prepared by adjusting the amounts of individual components as shown in Table 7 below, and the properties thereof were measured. The results are shown in Table 8 below.

TABLE 7

|  | Comparative Example 3-1 | Comparative Example 3-2 | Comparative Example 3-3 | Comparative Example 3-4 | Comparative Example 3-5 | Comparative Example 3-6 | Comparative Example 3-7 | Comparative Example 3-8 |
|---|---|---|---|---|---|---|---|---|
| Stearalkonium hectorite | 2 wt % | 2 wt % | 2 wt % | 2 wt % | 2 wt % | 2 wt % | 0.008 wt % | 7.5 wt % |
| Caprylic/capric triglyceride | 10 wt % | 10 wt % | 0.008 wt % | 36 wt % | 10 wt % | 10 wt % | 10 wt % | 10 wt % |
| Glycerin | 0.008 wt % | 46 wt % | 10 wt % | 10 wt % | 10 wt % | 10 wt % | 10 wt % | 10 wt % |
| Cetearyl olivate/ Sorbitan olivate | 3 wt % | 3 wt % | 3 wt % | 3 wt % | 0.008 wt % | 11 wt % | 3 wt % | 3 wt % |

TABLE 8

| Classification | Comparative Example 3-1 | Comparative Example 3-2 | Comparative Example 3-3 | Comparative Example 3-4 | Comparative Example 3-5 | Comparative Example 3-6 | Comparative Example 3-7 | Comparative Example 3-8 |
|---|---|---|---|---|---|---|---|---|
| Soft sensation | 3.65 | 3.6 | 3.3 | 3.2 | 3.5 | 3.2 | 3.3 | 4.2 |
| Moisturizing sensation (water) | 3.6 | 3.7 | 3.1 | 3.4 | 3.55 | 3.2 | 3.4 | 4.0 |
| Moisturizing sensation (oil) | 1.7 | 3.7 | 3.5 | 3.5 | 3.4 | 3.2 | 3.3 | 3.48 |
| Moisturizing persistence | 1.5 | 3.8 | 3.7 | 3.4 | 3.5 | 3.6 | 3.1 | 3.91 |
| Shape stability | 2.4 | 2.2 | 1.8 | 1.75 | 1.85 | 2.0 | 2.3 | 3.82 |

Evaluation criteria:
excellent 5,
good 4,
fair 3,
poor 2,
very poor 1

[Comparative Example 4] Evaluation of Properties of Stick-Type Formulation Depending on Preparation Conditions

[Comparative Example 4-1] Results Depending on Mixing Temperature of Glycerin and Cetearyl Olivate/Sorbitan Olivate Stick-type formulations were prepared at a mixing temperature of 58° C. in Comparative Example 4-1a and at 91° C. in Comparative Example 4-1b, and the properties thereof were measured.

In Comparative Example 4-1a, glycerin and cetearyl olivate were not dissolved, and thus an acceptable stick-type formulation was not made, and in Comparative Example 4-1b, the properties were almost the same as those in Example 1.

[Comparative Example 4-2] Evaluation of Properties of Stick-Type Formulation Depending on Preparation Temperature of Oil-Phase Part The preparation temperature of an oil-phase part was set to 50° C., 68° C., 86° C., and 90° C. in Comparative Examples 4-2a, 4-2b, 4-2c, and 4-2d, respectively. The properties of the resulting formulations were measured as in Test Example 1.

In Comparative Examples 4-2a and 4-2b, in which the mixing temperature was lower than 70° C., components such as wax, etc. were not sufficiently dissolved, and thus the stick formulation was not formed. On the other hand, when the temperature was higher than 90° C., a stable stick formulation was not formed.

The invention claimed is:

1. A method for preparing a stick-type cosmetic composition, the method comprising:
   a first stabilization step of forming a clay mineral dispersion by mixing 0.01 to 7 wt % of a clay mineral and 0.05 to 35 wt % of a first emollient based on a total weight of the stick-type cosmetic composition;
   a second stabilization step of forming a moisturizing component dispersion by mixing 0.01 to 45 wt % of a moisturizing component and 0.01 to 10 wt % of a first surfactant based on the total weight of the stick-type cosmetic composition; and a step of adding the clay mineral dispersion and the moisturizing component dispersion to an oil-phase part,
wherein the first stabilization step comprises stirring the clay mineral and the first emollient at 1000 to 2500 rpm.

2. The method of claim 1, wherein the step of adding the clay mineral dispersion and the moisturizing component dispersion to the oil-phase part comprises:
adding the clay mineral dispersion to the oil-phase part and then adding the moisturizing component dispersion thereto.

3. The method of claim 1, wherein the clay mineral comprises a platelet-shaped mineral.

4. The method of claim 1, wherein the first emollient comprises caprylic capric triglyceride.

5. The method of claim 1, wherein the moisturizing component is a water-soluble moisturizing component.

6. The method of claim 1, wherein the first surfactant comprises cetearyl olivate or sorbitan olivate.

7. The method of claim 1, wherein the first emollient is contained in an amount of 300 to 1000 parts by weight based on 100 parts by weight of a total weight of the clay mineral.

8. The method of claim 1, wherein the second stabilization step comprises mixing the moisturizing component and the first surfactant at 60 to 90° C.

9. The method of claim 1, wherein the oil-phase part comprises, based on the total weight of the stick-type cosmetic composition, 5 to 40 wt % of wax, 0.01 to 10 wt % of a second surfactant, and a remainder of a second emollient, which are mixed together.

10. The method of claim 3, wherein the platelet-shaped mineral comprises smectite.

11. The method of claim 5, wherein the water-soluble moisturizing component comprises glycerin.

12. The method of claim 9, wherein the oil-phase part further comprises butter or a preservative.

13. The method of claim 9, wherein the wax comprises at least one selected from the group consisting of candelilla wax, ozokerite, microcrystalline wax, and beeswax.

14. The method of claim 9, wherein the second surfactant comprises cetyl PEG/PPG-10/1-dimethicone or sorbitan olivate.

15. The method of claim 9, wherein the second emollient comprises at least one selected from the group consisting of *Macadamia ternifolia* seed oil, pentaerythrityl tetraisostearate, and caprylic capric triglyceride.

16. The method of claim 10, wherein the smectite comprises hectorite or bentonite.

17. The method of claim 16, wherein the hectorite is stearalkonium hectorite.

18. A method for preparing a stick-type cosmetic composition, the method comprising:
a first stabilization step of forming a clay mineral dispersion by mixing 0.01 to 7 wt % of a clay mineral and 0.05 to 35 wt % of a first emollient based on a total weight of the stick-type cosmetic composition;
a second stabilization step of forming a moisturizing component dispersion by mixing 0.01 to 45 wt % of a moisturizing component and 0.01 to 10 wt % of a first surfactant based on the total weight of the stick-type cosmetic composition; and
a step of adding the clay mineral dispersion and the moisturizing component dispersion to an oil-phase part,
wherein the second stabilization step comprises mixing the moisturizing component and the first surfactant at 60 to 90° C.

* * * * *